United States Patent
He et al.

(10) Patent No.: US 10,463,326 B2
(45) Date of Patent: Nov. 5, 2019

(54) C-ARM X-RAY APPARATUS WITH SURGICAL POSITIONING AND LINEAR NAVIGATION FUNCTION

(71) Applicant: HANGZHOU SANTAN MEDICAL TECHNOLOGY CO., LTD, Zhejiang (CN)

(72) Inventors: Bin He, Zhejiang (CN); Shigui Yan, Zhejiang (CN); Shuogui Xu, Zhejiang (CN); Liping Shen, Zhejiang (CN)

(73) Assignee: HANGZHOU SANTAN MEDICAL TECHNOLOGY CO., LTD, Zhejiang (CN)

( * ) Notice: Subject to any disclaimer, the term of this patent is extended or adjusted under 35 U.S.C. 154(b) by 195 days.

(21) Appl. No.: 15/560,162

(22) PCT Filed: May 29, 2015

(86) PCT No.: PCT/CN2015/080233
§ 371 (c)(1),
(2) Date: Sep. 21, 2017

(87) PCT Pub. No.: WO2016/169099
PCT Pub. Date: Oct. 27, 2016

(65) Prior Publication Data
US 2018/0092614 A1 Apr. 5, 2018

(30) Foreign Application Priority Data

Apr. 23, 2015 (CN) .......................... 2015 1 0196237
Apr. 23, 2015 (CN) ..................... 2015 2 0250205 U

(51) Int. Cl.
*A61B 6/12* (2006.01)
*A61B 6/00* (2006.01)
(Continued)

(52) U.S. Cl.
CPC .......... *A61B 6/4441* (2013.01); *A61B 6/4405* (2013.01); *A61B 90/37* (2016.02);
(Continued)

(58) Field of Classification Search
CPC ....... A61B 6/4441; A61B 6/4405; A61B 6/00; A61B 6/12; A61B 90/37
See application file for complete search history.

(56) References Cited

U.S. PATENT DOCUMENTS 5,483,572 A 1/1996 Hoornaert et al.
2017/0296273 A9 * 10/2017 Brown .................. A61B 90/13

FOREIGN PATENT DOCUMENTS

CN 2566804 Y 8/2003
CN 201642054 U 11/2010
(Continued)

OTHER PUBLICATIONS

"International Search Report (Form PCT/ISA/210)", dated Aug. 26, 2015, with English translation thereof, pp. 1-4.

*Primary Examiner* — David P Porta
*Assistant Examiner* — Shun Lee
(74) *Attorney, Agent, or Firm* — JCIPRNET

(57) ABSTRACT

A C-arm X-ray apparatus with a surgical positioning and linear navigation function is provided. The apparatus includes a C-arm, an image enhancer, an X-ray tube, a support frame, a trolley, a monitor and a central controller. The image enhancer is disposed at one end of the C-arm, and the X-ray tube is disposed at the other end of the C-arm which is mounted on the support frame and capable of rotationally sliding along the support frame, the support frame is mounted on the trolley and capable of sliding horizontally along the trolley, and the monitor and the central controller are electrically connected with the image enhancer and the X-ray tube, where a positioning module is
(Continued)

further disposed on the C-arm and cooperates with the image enhancer and the X-ray tube.

10 Claims, 4 Drawing Sheets

(51) Int. Cl.
*A61B 90/00* (2016.01)
*A61B 34/20* (2016.01)

(52) U.S. Cl.
CPC . *A61B 6/40* (2013.01); *A61B 6/46* (2013.01); *A61B 34/20* (2016.02); *A61B 90/361* (2016.02)

(56) References Cited

FOREIGN PATENT DOCUMENTS

| | | |
|---|---|---|
| CN | 202859934 U | 4/2013 |
| JP | 2003230554 A | 8/2003 |

\* cited by examiner

US 10,463,326 B2
C-ARM X-RAY APPARATUS WITH SURGICAL POSITIONING AND LINEAR NAVIGATION FUNCTION

CROSS-REFERENCE TO RELATED APPLICATION

This application is a 371 of international application of PCT application serial no. PCT/CN2015/080233, filed on May 29, 2015, which claims the priority benefit of China application no. 201510196237.6, filed on Apr. 23, 2015, and China application no. 201520250205.5, filed on Apr. 23, 2015. The entirety of each of the above-mentioned patent applications is hereby incorporated by reference herein and made a part of this specification.

BACKGROUND OF THE INVENTION

1. Field of the Invention

The present disclosure relates to a C-arm X-ray apparatus with surgical positioning and linear navigation function.

2. Description of Related Art

A movable X-ray apparatus having C-arm (hereinafter referred to as a C-arm X-ray apparatus) is a device commonly used in clinical surgery in hospitals, which integrates an X-ray generator and an image intensifier in two ends of a "C"-shaped arm frame structure, respectively. An image output from the image intensifier is transmitted to a television camera in a photoelectric coupling manner to form a video signal. The video signal may be displayed on a monitor in real time, so that a doctor may get visual information of an anatomical image for a patient and its dynamics during treatment, and the visual information may assist the doctor to accurately position a foreign body or a lesion tissue in vivo.

At present, a C-arm X-ray apparatus may only generate a perspective image for observing tissues and organs in vivo, and does not have surgical positioning and navigation function itself. As a minimally invasive surgical technology is developing, a surgical wound is getting smaller and smaller, and surgical effect depends largely on judging accuracy of a surgeon on a lesion without seeing the lesion directly. Therefore, a clinical demand of ex vivo lesion positioning and surgical navigation rises. At present, there are a few surgical positioning technologies and devices based on X-ray examination of a C-arm X-ray apparatus. If a C-arm X-ray apparatus has surgical positioning and navigation function itself, it may bring great convenience for an operation. Further, because intermediate process is reduced, it may have the advantage of accurate, fast and convenient positioning.

SUMMARY

In view of the aforementioned problems of the prior art, an object of the present disclosure is to provide a C-arm X-ray apparatus with surgical positioning and linear navigation function, which is capable of fast and accurately positioning a specific position of a foreign body or lesion tissue in a human body, increasing surgical safety, improving surgical accuracy, and reducing irradiation exposure and surgical injuries at the same time.

The C-arm X-ray apparatus with surgical positioning and linear navigation function includes a C-arm, an image intensifier, an X-ray tube, a support frame, a trolley, a monitor and a central controller. Where, the image intensifier is disposed at one end of the C-arm, the X-ray tube is arranged at the other end of the C-arm, the C-arm is arranged on the support frame and capable of rotationally sliding along the support frame, and the support frame is mounted on the trolley and capable of horizontally sliding along the trolley. The trolley, the monitor and the central controller are placed on the ground, and the monitor and the central controller both are electrically connected with the image intensifier and the X-ray tube. A positioning module is further disposed on the C-arm and cooperates with the image intensifier and the X-ray tube.

For the C-arm X-ray apparatus with surgical positioning and linear navigation function, the positioning module mainly comprises a first planar motion mechanism, a second planar motion mechanism and four connecting members which include a first connecting member, a second connecting member, a third connecting member as well as a fourth connecting member arranged at four corners of the first planar motion mechanism and the second planar motion mechanism;

the first planar motion mechanism comprises a first guide rail frame which is square and provided with a first x-direction motion rod and a first y-direction motion rod capable of sliding on the first guide rail frame, and the first x-direction motion rod is disposed perpendicularly to the first y-direction motion rod, the first x-direction motion rod slides in the x-direction of the first guide rail frame, and the first y-direction motion rod slides in the y-direction of the first guide rail frame. A first bearing seat is mounted on the first x-direction motion rod and the first y-direction motion rod in a way that the first x-direction motion rod is capable of driving the first bearing seat to move in the x-direction of the first guide rail frame, and the first y-direction motion rod is capable of driving the first bearing seat to move in the y-direction of the first guide rail frame. A first x-direction No. 1 belt pulley shaft is disposed on the first connecting member, and a first x-direction No. 2 belt pulley shaft is disposed on the second connecting member. A first x-direction synchronous belt is disposed on the first x-direction No. 1 belt pulley shaft as well as the first x-direction No. 2 belt pulley shaft, and fixedly connected with a slider at an end of the first x-direction motion rod. A first y-direction No. 1 belt pulley shaft is further disposed on the first connecting member, and a first y-direction No. 2 belt pulley shaft is disposed on the fourth connecting member. A first y-direction synchronous belt is disposed on the first y-direction No. 1 belt pulley shaft as well as the first y-direction No. 2 belt pulley shaft, and fixedly connected with a slider at an end of the first y-direction motion rod;

the second planar motion mechanism comprises a second guide rail frame which is square and provided with a second x-direction motion rod and a second y-direction motion rod capable of sliding on the second guide rail frame, and the second x-direction motion rod is disposed perpendicularly to the second y-direction motion rod, the second x-direction motion rod slides in the x-direction of the second guide rail frame, and the second y-direction motion rod slides in the y-direction of the second guide rail frame. A second bearing seat is mounted on the second x-direction motion rod and the second y-direction motion rod in a way that the second x-direction motion rod is capable of driving the second bearing seat to move in the x-direction of the second guide rail frame, and the second y-direction motion rod is capable of driving the second bearing seat to move in the y-direction of the second guide rail frame. A second x-direction No. 1 belt pulley shaft is further disposed on the first connecting member, and a second x-direction No. 2 belt pulley shaft is further disposed on the second connecting member. A second x-direction synchronous belt is disposed on the second x-direction No. 1 belt pulley shaft as well as the second x-direction No. 2 belt pulley shaft, and fixedly connected with a slider at an end of the second x-direction motion rod. A second y-direction No. 1 belt pulley shaft is further disposed on the first connecting member, and a second y-direction No. 2 belt pulley shaft is disposed on the fourth connecting member. A second y-direction synchronous belt is disposed on the second y-direction No. 1 belt pulley shaft as well as the second y-direction No. 2 belt pulley shaft, and fixedly connected with a slider at the end of the second y-direction motion rod;

the first planar motion mechanism is parallel to the second planar motion mechanism in a way that two ends of the first connecting member, the second connecting member, the third connecting member and the fourth connecting member are fixed to four corners of the first guide rail frame and the second guide rail frame, respectively. A first articulated bearing is mounted in the first bearing seat, and a second articulated bearing is mounted in the second bearing seat;

the first planar motion mechanism is provided with three first planar identifiers comprising three stainless steel balls which are an upper stainless steel ball, a lower stainless steel ball and a right stainless steel ball respectively disposed at upper, lower and right positions of the first y-direction motion rod. A distance between the first upper stainless steel ball and the first lower stainless steel ball is 80 mm, and a distance between the first lower stainless steel ball and the right stainless steel ball is 31 mm. The second planar motion mechanism is provided with three second planar identifiers comprising three stainless steel balls which are a second upper stainless steel ball, a second lower stainless steel ball and a left stainless steel ball respectively disposed at upper, lower and left positions of the second x-direction motion rod. A distance between the second upper stainless steel ball and the second lower stainless steel ball is 31 mm, and a distance between the second lower stainless steel ball and the left stainless steel ball is 80 mm. The first bearing seat is provided with a first planar center identifier comprising a stainless steel ball disposed on the first bearing seat. The second bearing seat is provided with a second planar center identifier comprising a stainless steel ball disposed on the second bearing seat. Positions of the three stainless steel balls as the first planar identifiers and the three stainless steel balls as the second planar identifiers are different from each other. And positions of the stainless steel ball as the first planar center identifier and the stainless steel ball as the second planar center identifier differ from each other;

a laser tube which is circular is directly disposed between the first articulated bearing and the second articulated bearing. A tail of the laser tube is mounted in the first articulated bearing, and a head of the laser tube is mounted in the second articulated bearing. An emitted laser of the laser tube is coaxial with the laser tube; and a driver is further disposed on the first connecting member where an input terminal of the driver is electrically connected with the central controller; an output terminal of the driver drives the first x-direction No. 1 belt pulley shaft, the first y-direction No. 1 belt pulley shaft, the second x-direction No. 1 belt pulley shaft, and the second y-direction No. 1 belt pulley shaft to move, and the output terminal of the driver is further connected with the tail of the laser tube and controls laser emission of the laser tube.

For the C-arm X-ray apparatus with surgical positioning and linear navigation function, the positioning module is fixedly mounted below the image intensifier and parallel to a bottom surface of the image intensifier.

For the C-arm X-ray apparatus with surgical positioning and linear navigation function, the first guide rail frame, the second guide rail frame, the first x-direction motion rod, the first y-direction motion rod, the second x-direction motion rod and the second y-direction motion rod are made of carbon fiber material which is not developable under X-ray.

For the C-arm X-ray apparatus with surgical positioning and linear navigation function, the following steps may be executed on the C-arm X-ray apparatus.

1) First, a matrix calibration image of a matrix calibration plate in a front view through the C-arm X-ray apparatus is acquired, and a signal associated with the matrix calibration image in a central controller is stored. Image processing is performed thereon for the matrix calibration image, and coordinate information of each of matrix points is recorded. Matrix calibration points comprising 552 stainless steel balls in a form of 24 rows and 23 columns have been arranged on the matrix calibration plate, and space between rows of stainless steel balls and space between columns of stainless steel balls are 6 mm.

2) The first y-direction motion rod and the second x-direction motion rod in the positioning module are moved to a central region of the positioning module in a way that both the first bearing seat and the second bearing seat are located in the center of the positioning module at this time. The first bearing seat and the first y-direction motion rod belong to the first planar motion mechanism of the positioning module, and the first y-direction motion rod is provided with three first planar identifiers. The second bearing seat and the second x-direction motion rod belong to the second planar motion mechanism of the positioning module, and the second x-direction motion rod is provided with three second planar identifiers. The first bearing seat is provided with a first planar center identifier, and the second bearing seat is provided with a second planar center identifier. A perspective image is acquired by using the C-arm X-ray apparatus. Image processing is performed for the perspective image by the central controller, and coordinate information of a corresponding point of each identifier in the image is recorded. The matrix calibration image in the central controller is superimposed on the current perspective image in a way that the number of matrices associated with the horizontal space between the first planar identifiers in the corresponding matrix calibration image is obtained. A first planar horizontal distance L1 corresponding to a unit matrix is calculated according to L1=the horizontal spacing of the first planar identifiers/the corresponding matrix number in the image. Similarly, a first planar longitudinal distance L2 corresponding to a unit matrix is calculated according to L2=the longitudinal spacing of the first planar identifiers/the corresponding matrix number in the image, a second planar horizontal distance L3 corresponding to a unit matrix is calculated according to L3=the horizontal spacing of the second planar identifiers/the corresponding matrix number in the image, and a second planar longitudinal distance L4 corresponding to a unit matrix is calculated according to L4=the longitudinal spacing of the second planar identifiers/the corresponding matrix number in the image.

3) A lesion perspective image is acquired when a lesion is placed under the C-arm X-ray apparatus. Image processing is performed by the central controller, and the coordinate information of the lesion point is recorded. Information of the perspective image acquired in step 2 is superimposed on the lesion perspective image, and distances between the first planar center identifier and the second planar center to the lesion point are respectively obtained, which are expressed through the number of matrices N1, N2, N3 and N4. Execution distances L1X, L1Y, L2X and L2Y of the positioning module in different directions are calculated, where L1X=L1×N1, L1Y=L2×N2, L2X=L3×N3, and L2Y=L4×N4. A computational result is sent to the driver of the positioning module through the central controller in a way that the laser points to the lesion point after the driver completes the execution, that is, positioning is completed, and an operator may locate the lesion point along the direction of the laser.

The C-arm X-ray apparatus with surgical positioning and linear navigation function according to the present disclosure changes the use of a traditional C-arm X-ray apparatus, so that a C-arm X-ray apparatus has positioning function and is capable of helping a doctor to accurately and fast position a lesion point to bring new revolutionary changes to the use of C-arm X-ray apparatuses.

The C-arm X-ray apparatus with surgical positioning and linear navigation function according to the present disclosure is simple in operation. Positioning may be completed in such a way that a user performs X-ray examination on a lesion part by the C-arm X-ray apparatus, selects a lesion point according to a perspective image, and clicks on the lesion point with a mouse. Compared with existing surgical positioning technologies and devices based on a perspective image of a C-arm X-ray apparatus, the C-arm X-ray apparatus according to the present disclosure has surgical positioning and navigation function itself. Because an intermediate process is reduced, the C-arm X-ray apparatus with surgical positioning and linear navigation function has the advantage of accurately, fast and conveniently positioning, bringing great convenience for operation.

On the premise of having surgical positioning and linear navigation function, the C-arm X-ray apparatus with surgical positioning and linear navigation function according to the present disclosure still retains its traditional X-ray examination function. In particular, when positioning is not needed, it may be switched to a non-positioning mode, and the positioning module is moved to a corner. At this time, the C-arm X-ray apparatus with surgical positioning and linear navigation function according to the present disclosure may perform X-ray examination for a lesion without interfering with a perspective image.

The C-arm X-ray apparatus with surgical positioning and linear navigation function according to the present disclosure enables a doctor to perform operations such as minimal invasion, intervention and the like fast and accurately with high accuracy and good stability, so as to improve surgical safety, shorten surgical time, and reduce irradiation exposure caused by repeated X-ray examinations, thereby decreasing risk of tissue injuries and complications.

DETAILED DESCRIPTION OF THE EMBODIMENTS

Figure 1:
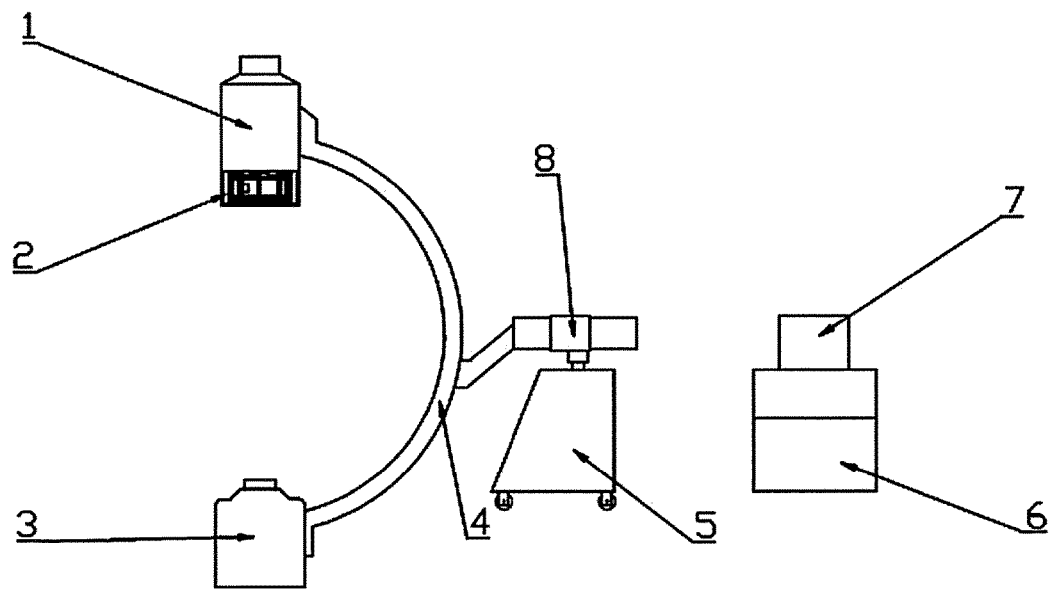
FIG. 1 illustrates a schematic diagram of a C-arm X-ray apparatus with surgical positioning and linear navigation function.
Figure 2:
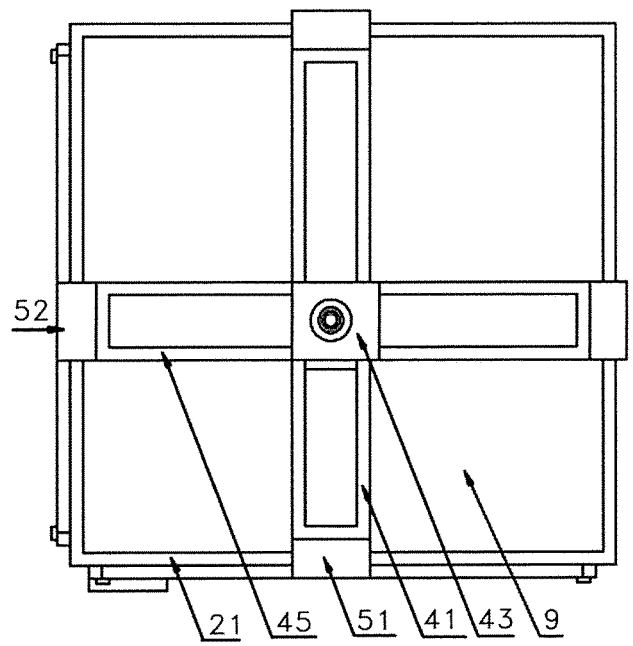
FIG. 2 illustrates a schematic diagram of a first planar motion mechanism of a positioning module.
Figure 3:
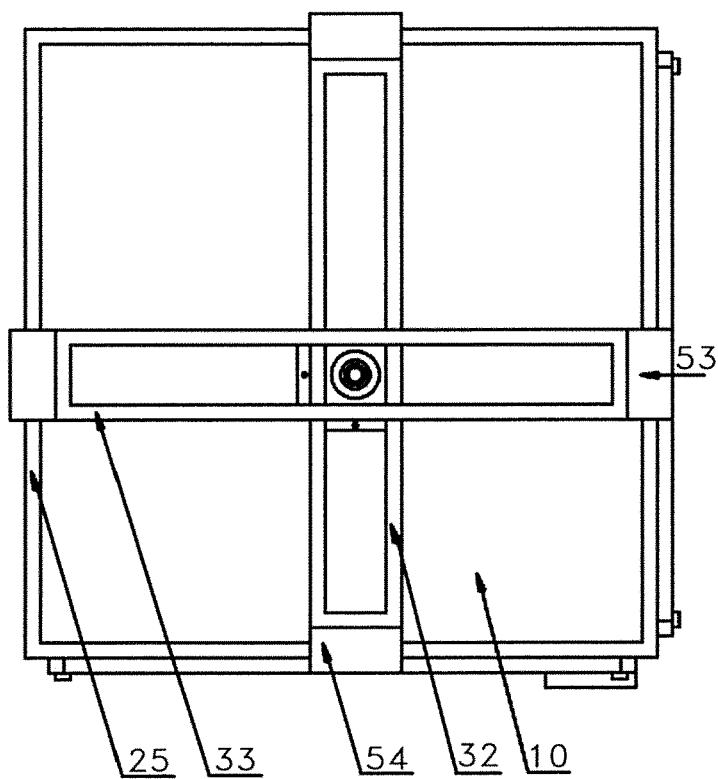
FIG. 3 illustrates a schematic diagram of a second planar motion mechanism of a positioning module.
Figure 4:
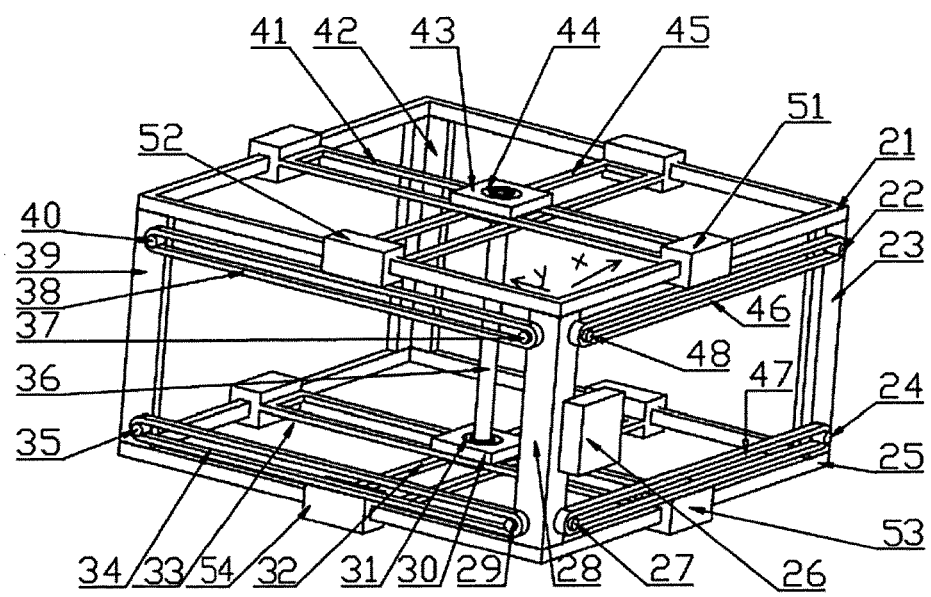
FIG. 4 illustrates a schematic diagram of a positioning module.
Figure 5:
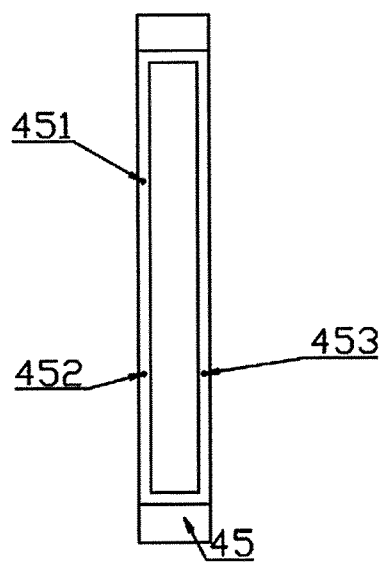
FIG. 5 illustrates a schematic diagram of first planar identifier points.
Figure 6:
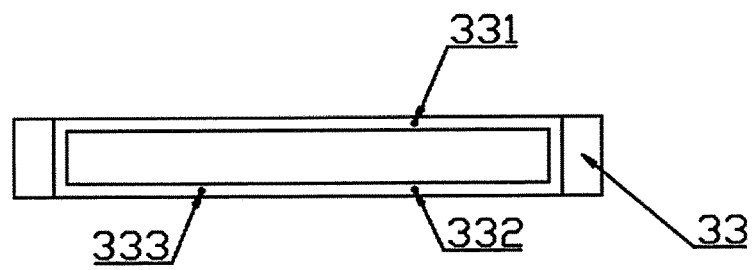
FIG. 6 illustrates a schematic diagram of second planar identifier points.
Figure 7:
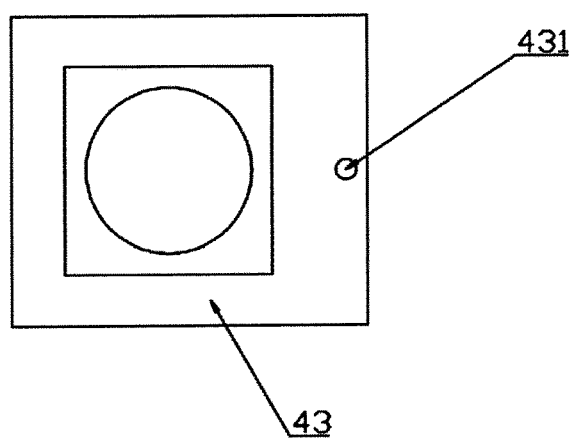
FIG. 7 illustrates a schematic diagram of a first planar center identifier point.
Figure 8:
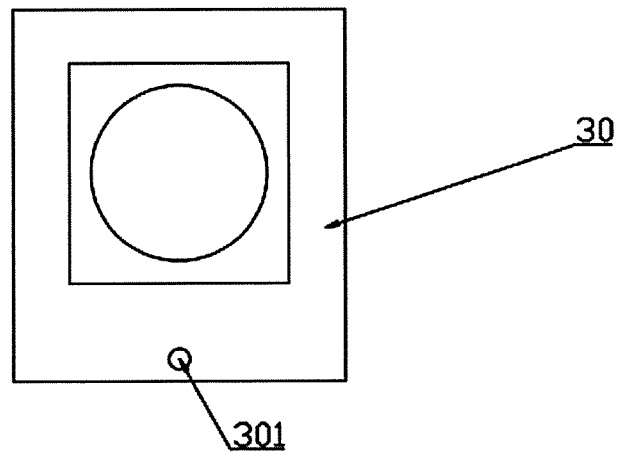
FIG. 8 illustrates a schematic diagram of a second planar center identifier point.
Figure 9:
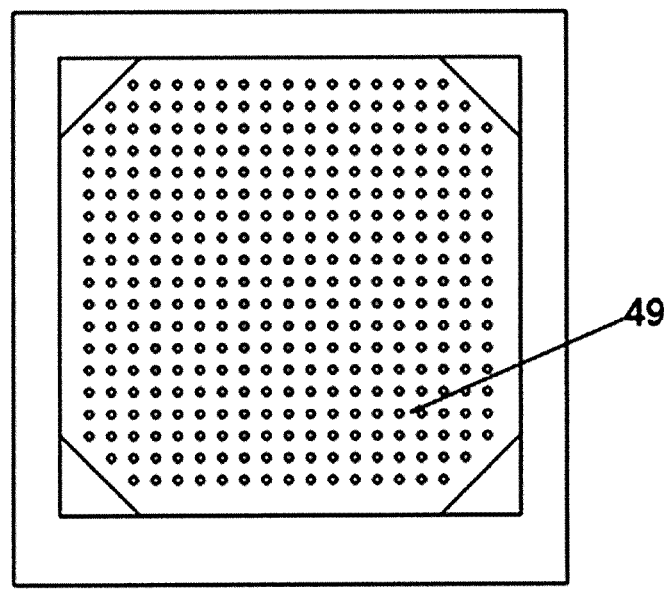
FIG. 9 illustrates a perspective image of a matrix calibration plate in a front view;
where 1-image intensifier, 2-positioning module, 3-X-ray tube, 4-C-arm, 5-trolley, 6-central controller, 7-monitor, 8-support frame, 9-first planar motion mechanism, 10-second planar motion mechanism, 21-first guide rail frame, 22-first x-direction No. 2 belt pulley shaft, 23-second connecting member, 24-second x-direction No. 2 belt pulley shaft, 25-second guide rail frame, 26-driver, 27-second x-direction No. 1 belt pulley shaft, 28-first connecting member, 29-second y-direction No. 1 belt pulley shaft, 30-second bearing seat, 31-second articulated bearing, 32-second y-direction motion rod, 33-second x-direction motion rod, 34-second y-direction synchronous belt, 35-second y-direction No. 2 belt pulley shaft, 36-laser tube, 37-first y-direction No. 1 belt pulley shaft, 38-first y-direction synchronous belt, 39-fourth connecting member, 40-first y-direction No. 2 belt pulley shaft, 41-first x-direction motion rod, 42-third connecting member, 43-first bearing seat, 44-first articulated bearing, 45-first y-direction motion rod, 46-first x-direction synchronous belt, 47-second x-direction synchronous belt, 48-first x-direction No. 1 belt pulley shaft, 49-matrix calibration image, 451-first upper stainless steel ball, 452-first lower stainless steel ball, 453-right stainless steel ball, 331-second upper stainless steel ball, 332-second lower stainless steel ball, 333-left stainless steel ball, 431-first planar center identifier, 301-second planar center identifier, 51-slider, 52-slider, 53-slider, and 54-slider.

The present disclosure will now be further described with reference to the accompanying drawings:

According to the present disclosure, a C-arm X-ray apparatus with surgical positioning and linear navigation function retains functions of a traditional C-arm X-ray apparatus, and further includes a positioning module to change usage of a traditional C-arm X-ray apparatus by making the C-arm X-ray apparatus have a positioning function. Thus, the C-arm X-ray apparatus may assist a doctor in accurately and quickly positioning a lesion point, thereby bringing new revolutionary changes to usage of C-arm X-ray apparatuses.

According to the present disclosure, the C-arm X-ray apparatus with surgical positioning and linear navigation function includes a C-arm 4, an image intensifier 1, an X-ray tube 3, a support frame 8, a trolley 5, a monitor 7 and a central controller 6. The image intensifier 1 is disposed at one end of the C-arm 4. The X-ray tube 3 is disposed at the other end of the C-arm 4. The C-arm 4 is mounted on the support frame 8 and capable of rotationally sliding along the support frame. The support frame 8 is mounted on the trolley 5 and capable of sliding horizontally along the trolley. The trolley, the monitor and the central controller are placed on the ground. And the monitor and the central controller are electrically connected with the image intensifier and the X-ray tube. In addition to existing functions of the prior art C-arm X-ray apparatus, the central controller further has functions such as positioning data processing and sending a controlling signal. A positioning module is further disposed on the C-arm and cooperates with the image intensifier and the X-ray tube.

The positioning module mainly comprises a first planar motion mechanism 9, a second planar motion mechanism 10 and four connecting members which include a first connecting member 28, a second connecting member 23, a third connecting member 42 and a fourth connecting member 39. The four connecting members are disposed at four corners of the first planar motion mechanism and the second planar motion mechanism.

The first planar motion mechanism comprises a first guide rail frame 21 which is square and provided with a first x-direction motion rod 41 and a first y-direction motion rod 45 capable of sliding. The first x-direction motion rod 41 is disposed perpendicularly to the first y-direction motion rod 45. The first x-direction motion rod 41 slides in the x-direction of the first guide rail frame 21, and the first y-direction motion rod 45 slides in the y-direction of the first guide rail frame 21. A first bearing seat 43 is mounted on the first x-direction motion rod 41 and the first y-direction motion rod 45 in a way that the first x-direction motion rod 41 is capable of driving the first bearing seat 43 to move in the x-direction of the first guide rail fame 21, and the first y-direction motion rod 45 is capable of driving the first bearing seat 43 to move in the y-direction of the first guide rail frame 21. A first x-direction No. 1 belt pulley shaft 48 is disposed on the first connecting member 28. A first x-direction No. 2 belt pulley shaft 22 is disposed on the second connecting member 23. A first x-direction synchronous belt 46 is disposed on the first x-direction No. 1 belt pulley shaft 48 as well as the first x-direction No. 2 belt pulley shaft 22 and fixedly connected with a slider 51 at an end of the first x-direction motion rod 41. A first y-direction No. 1 belt pulley shaft 37 is further disposed on the first connecting member 28. A first y-direction No. 2 belt pulley shaft 40 is disposed on the fourth connecting member 39. A first y-direction synchronous belt 38 is disposed on the first y-direction No. 1 belt pulley shaft 37 as well as the first y-direction No. 2 belt pulley shaft 40 and fixedly connected with a slider 52 at an end of the first y-direction motion rod 45.

The second planar motion mechanism 10 comprises a second guide rail frame 25 which is square and provided with a second x-direction motion rod 33 and a second y-direction motion rod 32 capable of sliding. The second x-direction motion rod 33 is disposed perpendicularly to the second y-direction motion rod 32. The second x-direction motion rod 33 slides in the x-direction of the second guide rail frame 25, and the second y-direction motion rod 32 slides in the y-direction of the second guide rail frame 25. A second bearing seat 30 is mounted on the second x-direction motion rod 33 and the second y-direction motion rod 32 in a way that and the second x-direction motion rod 33 is capable of driving the second bearing seat 30 to move in the x-direction of the second guide rail frame 25, and the second y-direction motion rod 32 is capable of driving the second bearing seat 30 to move in the y-direction of the second guide rail frame 25. A second x-direction No. 1 belt pulley shaft 27 is further disposed on the first connecting member 28. A second x-direction No. 2 belt pulley shaft 24 is further disposed on the second connecting member 23. A second x-direction synchronous belt 47 is disposed on the second x-direction No. 1 belt pulley shaft 27 as well as the second x-direction No. 2 belt pulley shaft 24 and fixedly connected with a slider 53 at an end of the second x-direction motion rod 33. A second y-direction No. 1 belt pulley shaft 29 is further disposed on the first connecting member 28. A second y-direction No. 2 belt pulley shaft 35 is disposed on the fourth connecting member 39. A second y-direction synchronous belt 34 is disposed on the second y-direction No. 1 belt pulley shaft 29 as well as the second y-direction No. 2 belt pulley shaft 35 and fixedly connected with a slider 54 at an end of the second y-direction motion rod 32.

The first planar motion mechanism 9 is parallel to the second planar motion mechanism 10 in a way that two ends of the first connecting member 28, the second connecting member 23, the third connecting member 42 and the fourth connecting member 39 are fixed to four corners of the first guide rail frame 21 and the second guide rail frame 25, respectively. A first articulated bearing 44 is mounted in the first bearing seat 43, and a second articulated bearing 31 is mounted in the second bearing seat 30.

The first planar motion mechanism 9 is provided with three first planar identifiers comprising three stainless steel balls respectively disposed at upper, lower and right positions of the first y-direction motion rod 45, i.e., a first upper stainless steel ball 451, a first lower stainless steel ball 452 and a right stainless steel ball 453, where a distance between the first upper stainless steel ball 451 and the first lower stainless steel ball 452 is 80 mm, and a distance between the first lower stainless steel ball 452 and the right stainless steel ball 453 is 31 mm. The second planar motion mechanism 10 is provided with three second planar identifiers comprising three stainless steel balls respectively at upper, lower and left positions of the second x-direction motion rod 33, i.e., a second upper stainless steel ball 331, a second lower stainless steel ball 332 and a left stainless steel ball 333, where a distance between the second upper stainless steel ball 331 and the second lower stainless steel ball 332 is 31 mm, and a distance between the second lower stainless steel ball 332 and the left stainless steel ball 333 is 80 mm. The first bearing seat 43 is provided with a first planar center identifier 431 including a stainless steel ball disposed on the first bearing seat 43. The second bearing seat 30 is provided with a second planar center identifier 301 including a stainless steel ball disposed on the second bearing seat 30. Where positions of the three stainless steel balls as the first planar identifiers and the three stainless steel balls as the second planar identifiers are different from each other. And positions of the stainless steel ball as the first planar center identifier 431 and the stainless steel ball as the second planar center identifier 301 are different from each other.

A laser tube 36 which is a circular tube is directly disposed between the first articulated bearing 44 and the second articulated bearing 31. A tail of the laser tube 36 is mounted in the first articulated bearing 44. A head of the laser tube 36 is mounted in the second articulated bearing 31. And an emitted laser of the laser tube 36 is coaxial with the laser tube 36.

A driver 26 is further disposed on the first connecting member 28. An input terminal of the driver 26 is electrically connected with the central controller 6. An output terminal of the driver 26 drives the first x-direction No. 1 belt pulley shaft 45, the first y-direction No. 1 belt pulley shaft 37, the second x-direction No. 1 belt pulley shaft 27 and the second y-direction No. 1 belt pulley shaft 29 to move. And the output terminal of the driver 26 is further connected with the tail of the laser tube 36 to control laser emission of the laser tube 36.

When being specifically installed, the positioning module is fixedly mounted below the image intensifier and parallel to a bottom surface of the image intensifier.

According to the present disclosure, the first guide rail frame 21, the second guide rail frame 25, the first x-direction motion rod 41, the first y-direction motion rod 45, the second x-direction motion rod 33 and the second y-direction motion rod 32 are made of carbon fiber material which is not developable under X-ray.

According to examples of the present disclosure, the following steps are executed on a C-arm X-ray apparatus:

1) First, a matrix calibration image 49 of a matrix calibration plate in a front view through the C-arm X-ray apparatus is acquired, and a signal associated with a matrix calibration image in the central controller 6 is stored. Image processing is performed for the matrix calibration image, and coordinate information of each of matrix points is recorded, where the matrix calibration points comprises 522 stainless steel balls disposed on the matrix calibration plate in a form of 24 rows and 23 columns where space between rows and space between columns are 6 mm.

2) The first y-direction motion rod 45 and the second x-direction motion rod 33 in the positioning module 2 are moved to a central region of the positioning module in a way that the first bearing seat 43 and the second bearing seat 30 are located in the center of the positioning module, where the first bearing seat 43 and the first y-direction motion rod 45 belong to the first planar motion mechanism 9 of the positioning module and the first y-direction motion rod 45 is provided with three first planar identifiers. The second bearing seat 30 and the second x-direction motion rod 33 belong to the second planar motion mechanism 10 of the positioning module and the second x-direction motion rod 33 is provided with three second planar identifiers. The first bearing seat 43 is provided with a first planar center identifier, and the second bearing seat 30 is provided with a second planar center identifier. A perspective image is acquired by using the C-arm X-ray apparatus. The image processing is performed for the perspective image by the central controller 6, and coordinate information of a point corresponding to each identifier point in the image is recorded. Information of the matrix calibration image 49 in the central controller 6 is superimposed on the current perspective image in a way that the number of matrices associated with a horizontal space between the first planar identifiers in the corresponding matrix calibration image is obtained. A first planar horizontal distance L1 is calculated corresponding to a unit matrix according to L1=the horizontal space between the first planar identifiers/the corresponding number of matrices in the image; A first planar longitudinal distance L2 is acquired corresponding to a unit matrix according to L2=the longitudinal space between the first planar identifiers/the corresponding number of matrices in the image; a second planar horizontal distance L3 is calculated according to L3=the horizontal space between the second planar identifiers/the corresponding number of matrices in the image; and a second planar longitudinal distance L4 is calculated according to L4=the longitudinal space between the second planar identifiers/the corresponding number of matrices in the image.

3) A lesion perspective image is acquired when a lesion is placed under the C-arm X-ray apparatus. The image processing is performed through the central controller 6. Coordinate information of a lesion point is recorded. Information of the perspective image acquired in step 2 is superimposed on the lesion perspective image, and distances from the first planar center identifier 431 and the second planar center identifier 301 to the lesion point are respectively obtained. The distances above are expressed through the number of matrices N1, N2, N3 and N4. Execution distances L1X, L1Y, L2X and L2Y of the positioning module in different directions are calculated, where L1X=L1×N1, L1Y=L2×N2, L2X=L3×N3, and L2Y=L4×N4, and a computational result is sent to the driver of the positioning module through the central controller in a way that the laser points to the lesion point after the driver completes positioning, and an operator may find the lesion point along a direction of the laser.

A method according to the present disclosure is as follows:

a C-arm X-ray apparatus with surgical positioning and linear navigation function is moved to be above a lesion point. A lesion perspective image is acquired by using the C-arm X-ray apparatus with surgical positioning and linear navigation function. A mouse is moved to the lesion point on the lesion perspective image and click on the lesion point. Thus, the positioning module automatically aligns the laser beam emitted by the laser tube 36 with the lesion point. Till now, the system positioning is successfully completed.

The C-arm X-ray apparatus with surgical positioning and linear navigation function according to the present disclosure has changed a usage of a traditional C-arm X-ray apparatus by making a C-arm X-ray apparatus have a positioning function. Thus, the C-arm X-ray apparatus is capable of assisting a doctor in accurately and quickly positioning a lesion point, thereby bringing new revolutionary changes to the usage of the C-arm X-ray apparatus.

According to the present disclosure, the C-arm X-ray apparatus with surgical positioning and linear navigation function is simple in operation. The positioning may be completed in such a way that a user performs X-ray examination on a lesion region by the C-arm X-ray apparatus, selects the lesion point according to the perspective image, and clicks on the lesion point with a mouse. Compared with existing surgical positioning technologies and devices based on a perspective image of the C-arm X-ray apparatus, the C-arm X-ray apparatus according to the present disclosure itself has surgical positioning and navigation function, so as to reduce an intermediate process. Further, the C-arm X-ray apparatus has an advantage of accurately, quickly and conveniently positioning, thereby bringing great convenience for operation.

On the premise of having surgical positioning and linear navigation functions, the C-arm X-ray apparatus with surgical positioning and linear navigation function according to the present disclosure still retains its traditional X-ray examination function. In particular, when positioning is not needed, it may be switched to a non-positioning mode, and the positioning module is moved to a corner. According to the present disclosure, the C-arm X-ray apparatus with surgical positioning and linear navigation function may perform X-ray examination for the lesion without interference with the perspective image.

By means of a C-arm X-ray apparatus with surgical positioning and linear navigation function according to the present disclosure, doctors are capable of quickly and accurately performing operations such as minimal invasion, intervention and the like with high accuracy and good stability, so as to improve surgical safety, shorten surgical time, and reduce irradiation exposure caused by repeated X-ray examinations, thereby decreasing risk of tissue injuries and complications.

What is claimed is:

1. A C-arm X-ray apparatus with surgical positioning and linear navigation function, comprising:
   a trolley;
   a support frame mounted on the trolley and capable of sliding horizontally along the trolley;

a C-arm mounted on the support frame and capable of rotationally sliding along the support frame;
an image enhancer disposed at one end of the C-arm;
an X-ray tube disposed at the other end of the C-arm;
a monitor electrically connected with the image enhancer and the X-ray tube;
a central controller electrically connected with the image enhancer and the X-ray tube, wherein the trolley, the monitor and the central controller are placed on the ground; and
a positioning module disposed on the C-arm and cooperates with the image enhancer and the X-ray tube,
wherein the positioning module comprises:
a first planar motion mechanism;
a second planar motion mechanism being parallel to the first planar motion mechanism; and
four connecting members respectively disposed between and connecting four corners of the first planar motion mechanism and the second planar motion mechanism, wherein the four connecting members comprises a first connecting member, a second connecting member, a third connecting member as well as a fourth connecting member arranged in order;
wherein the first planar motion mechanism, comprising:
 a first guide rail frame in a square shape;
 a first x-direction motion rod disposed on the first planar motion mechanism to be slidable on a x-direction of the first planar motion mechanism;
 a first y-direction motion rod disposed on the first planar motion mechanism to be slidable on a y-direction of the first planar motion mechanism, wherein the x-direction is perpendicular to the y-direction;
 first planar identifiers comprising a first upper stainless steel ball, a first lower stainless steel ball and a right stainless steel ball respectively disposed at upper, lower and right positions of the first y-direction motion rod;
 a first bearing seat mounted on the first x-direction motion rod and the first y-direction motion rod in a way that the first x-direction motion rod is capable of driving the first bearing seat to move in the x-direction of the first guide rail frame, and the first y-direction motion rod is capable of driving the first bearing seat to move in the y-direction of the first guide rail frame;
 a first articulated bearing mounted in the first bearing seat;
 a first planar center identifier disposed on the first bearing seat;
 a first x-direction No. 1 belt pulley shaft disposed on the first connecting member;
 a first x-direction No. 2 belt pulley shaft disposed on the second connecting member;
 a first x-direction synchronous belt disposed on the first x-direction No. 1 belt pulley shaft as well as the first x-direction No. 2 belt pulley shaft and fixedly connected with a slider at an end of the first x-direction motion rod;
 a first y-direction No. 1 belt pulley shaft disposed on the first connecting member;
 a first y-direction No. 2 belt pulley shaft disposed on the fourth connecting member; and
 a first y-direction synchronous belt disposed on the first y-direction No. 1 belt pulley shaft as well as the first y-direction No. 2 belt pulley shaft and fixedly connected with a slider at an end of the first y-direction motion rod;
wherein the second planar motion mechanism, comprising:
 a second guide rail frame in a square shape;
 a second x-direction motion rod disposed on the second planar motion mechanism to be slidable on an x-direction of the second planar motion mechanism;
 a second y-direction motion rod disposed on the second planar motion mechanism to be slidable on a y-direction of the second planar motion mechanism, wherein the x-direction is perpendicular to the y-direction;
 second planar identifiers comprising a second upper stainless steel ball, a second lower stainless steel ball and a left stainless steel ball respectively disposed at upper, lower and left positions of the second x-direction motion rod, wherein the positions of the first planar identifiers and the second planar identifiers are different from each other;
 a second bearing seat mounted on the second x-direction motion rod and the second y-direction motion rod in a way that the second x-direction motion rod is capable of driving the second bearing seat to move in the x-direction of the second guide rail frame, and the second y-direction motion rod is capable of driving the second bearing seat to move in the y-direction of the second guide rail frame;
 a second articulated bearing mounted in the second bearing seat;
 a second planar center identifier disposed on the second bearing seat, wherein the position of the first planar center identifier and the second planar center identifier are different from each other;
 a second x-direction No. 1 belt pulley shaft disposed on the second connecting member;
 a second x-direction No. 2 belt pulley shaft disposed on the second connecting member; and
 a second x-direction synchronous belt disposed on the second x-direction No. 1 belt pulley shaft as well as the second x-direction No. 2 belt pulley shaft and fixedly connected with a slider at an end of the second x-direction motion rod;
 a second y-direction No. 1 belt pulley shaft disposed on the second connecting member;
 a second y-direction No. 2 belt pulley shaft disposed on the fourth connecting member; and
 a second y-direction synchronous belt disposed on the second y-direction No. 1 belt pulley shaft as well as the second y-direction No. 2 belt pulley shaft and fixedly connected with a slider at an end of the second y-direction motion rod;
a laser tube disposed between the first and the second articulated bearings, wherein a tail of the laser tube is mounted in the first articulated bearing and a head of the laser tube is mounted in the second articulated bearing;
an emitted laser disposed in the laser tube, wherein the emitted laser is coaxial with the laser tube; and
a driver disposed on the first connecting member, wherein an input terminal of the driver is electrically connected to the central controller, and an output terminal of the driver is connected to the tail of the laser tube to control the laser emission of the laser tube and drives the motions of the first x-direction No. 1 belt pulley shaft, the first y-direction No. 1 belt pulley shaft, the second x-direction No. 1 belt pulley shaft, and the second y-direction No. 1 belt pulley shaft.

2. The C-arm X-ray apparatus of claim 1, wherein the positioning module is fixedly mounted below the image enhancer and parallel to a bottom surface of the image enhancer.

3. The C-arm X-ray apparatus of claim 1, wherein a distance between the first upper stainless steel ball and the first lower stainless steel ball is 80 mm, and a distance between the first lower stainless steel ball and the right stainless steel ball is 31 mm.

4. The C-arm X-ray apparatus of claim 1, wherein a distance between the second upper stainless steel ball and the second lower stainless steel ball is 31 mm, and a distance between the second lower stainless steel ball and the left stainless steel ball is 80 mm.

5. The C-arm X-ray apparatus of claim 1, wherein the first planar center identifier comprises a stainless steel ball.

6. The C-arm X-ray apparatus of claim 1, wherein the second planar center identifier comprises a stainless steel ball.

7. The C-arm X-ray apparatus of claim 1, wherein the laser tube is a circular tube.

8. The C-arm X-ray apparatus of claim 1, wherein the first guide rail frame, the second guide rail frame, the first x-direction motion rod, the first y-direction motion rod, the second x-direction motion rod and the second y-direction motion rod are made of carbon fiber material which is not developable under X-ray.

9. A method of operating the C-arm X-ray apparatus of claim 1, the method comprising:
  acquiring a matrix calibration image of a matrix calibration plate in a front view through the C-arm X-ray apparatus;
  storing a signal associated with the matrix calibration image in the central controller;
  performing image processing for the matrix calibration image to record coordinate information of each of matrix calibration points on the matrix calibration plate;
  moving the first y-direction motion rod and the second x-direction motion rod in the positioning module to a central region of the positioning module in a way that the first bearing seat and the second bearing seat are located in the center of the positioning module;
  acquiring a perspective image through the C-arm X-ray apparatus;
  performing image processing for the perspective image by the central controller to record the coordinate information of a point corresponding to each of the first planar identifiers, the first planar center identifier, the second planar identifiers, and the second planar center identifier in the image;
  superimposing information of the matrix calibration image in the central controller on information of the current perspective image to obtain the number of matrices associated with horizontal space between the first planar identifiers in the corresponding matrix calibration image;
  calculating a first planar horizontal distance corresponding to a unit matrix L1 according to L1=the horizontal space between the first planar identifiers/the corresponding number of matrices in the image;
  calculating a first planar longitudinal distance corresponding to the unit matrix L2 acquired according to L2=longitudinal space between the first planar identifiers/the corresponding number of matrices in the image;
  calculating a second planar horizontal distance corresponding to the unit matrix L3 according to L3=horizontal space between the second planar identifiers/the corresponding number of matrices in the image;
  calculating a second planar longitudinal distance L4 is acquired according to L4=longitudinal space between the second planar identifiers/the corresponding number of matrices in the image;
  acquiring a lesion perspective image when a lesion is placed under the C-arm X-ray apparatus;
  perform image processing through the central controller to record coordinate information of a lesion point of the lesion;
  superimposing the information of the perspective image on the lesion perspective image;
  respectively obtaining distances from the first planar center identifier and the second planar center identifier to the lesion point, which are expressed through the number of matrices N1, N2, N3 and N4;
  calculating execution distances L1X, L1Y, L2X and L2Y of the positioning module in different directions, wherein L1X=L1×N1, L1Y=L2×N2, L2X=L3×N3, and L2Y=L4×N4; and
  sending a computational result to the driver of the positioning module by the controller, so that the laser the laser points to the lesion point after the driver completes positioning, and an operator can find the lesion point along a direction of the laser.

10. The method of claim 9, wherein the matrix calibration points comprise 552 stainless steel balls disposed on the matrix calibration plate in a matrix form having 24 rows and 23 columns, and spaces between adjacent rows and columns of stainless steel balls are 6 mm.

* * * * *